United States Patent [19]

Schroeder

[11] Patent Number: 4,937,378
[45] Date of Patent: Jun. 26, 1990

[54] PURIFICATION OF CRUDE ISOPHTHALIC ACID

[75] Inventor: Hobe Schroeder, Warrenville, Ill.

[73] Assignee: Amoco Corporation, Chicago, Ill.

[21] Appl. No.: 421,560

[22] Filed: Oct. 13, 1989

[51] Int. Cl.⁵ .............................. C07C 51/487
[52] U.S. Cl. ........................ 562/487; 560/78; 562/485
[58] Field of Search ........................ 562/487

[56] References Cited

U.S. PATENT DOCUMENTS

| | | | |
|---|---|---|---|
| 3,584,039 | 6/1971 | Meyer | 562/487 X |
| 3,726,915 | 4/1973 | Pohlmann | 562/487 |
| 4,405,809 | 9/1983 | Steck et al. | 562/487 |
| 4,467,110 | 8/1984 | Puskas et al. | 562/487 |
| 4,626,598 | 12/1986 | Packer et al. | 562/487 |

Primary Examiner—Werren B. Lone
Assistant Examiner—Vera C. Clarke
Attorney, Agent, or Firm—James R. Henes; William H. Magidson; Ralph C. Medhurst

[57] ABSTRACT

Solutions of crude isophthalic acid are purified by hydrogenation to provide purified isophthalic acid having a predetermined color scale b*-value or optical density.

28 Claims, No Drawings

PURIFICATION OF CRUDE ISOPHTHALIC ACID

BACKGROUND OF THE INVENTION

1. Field of the Invention

This invention relates generally to a method for the catalytic purification by hydrogenation of crude isophthalic acid dissolved in a polar solvent, and more particularly concerns the use in such purification of a catalyst comprising either a single Group VIII noble metal component other than a palladium-containing component or a plurality of Group VIII noble metal components comprising at least two of palladium-, platinium, rhodium-, ruthenium-, osmium, and iridium-containing components, and the modulation of the solution hydrogen concentration during hydrogenation.

2. Discussion of the Prior Art

Polymer grade or "purified" isophthalic acid is one of the starting materials which are employed in the manufacture of unsaturated polyesters. Purified isophthalic acid is derived from relatively less pure, technical grade or "crude" isophthalic acid by purification of the latter utilizing hydrogen and a noble metal catalyst, of the type described in Meyer, U.S. Pat. No. 3,584,039 or Stech et al., U.S. Pat. No. 4,405,809 for the purification of crude terephthalic acid. In the purification process, the crude isophthalic acid is dissolved in water at an elevated temperature, and the resulting solution is hydrogenated, preferably in the presence of a hydrogenation catalyst containing a noble metal, typically palladium, on a carbon support, as described in Pohlmann, U.S. Pat. No. 3,726,915 for the purification of crude terephthalic acid. This hydrogenation step converts the various color bodies present in the crude isophthalic acid to colorless products.

However, even after the aforesaid purification, the purified isophthalic acid product contains color bodies. Therefore, it is highly desirable to reduce the concentration of such color bodies that remain in purified isophthalic acid. The color level of purified isophthalic acid product is generally measured directly either by measuring the optical density of solutions of purified isophthalic acid or the b*-value of the solid purified isophthalic acid itself. The optical density of purified isophthalic acid is measured as the absorbance of light at 340 and 400 nanometers (nm) in its basic solution in a solvent such as sodium hydroxide or ammonium hydroxide.

The measurement of the b*-value of a solid on the Hunter Color Scale is described in Hunter, *The Measurement of Appearance*, Chapter 8, pp. 102-132, John Wiley & Sons, N.Y., N.Y. (1975), and in Wyszecki et al., *Color Science, Concepts and Methods, Quantitative Data and Formulae*, 2d Ed., pp. 166-168, John Wiley & Sons, N.Y., N.Y. (1982).

More specifically, the b*-value of purified isophthalic acid can be determined using, for example, a Diano Match Scan Spectrophotometer as follows. Purified isophthalic acid is pressed into a pellet having a thickness of about 0.25 inch and a diameter of about 1 inch. The pellet is then irradiated with white light that has been UV-filtered. The spectrum of the visible light reflected from the sample is determined and tristimulus values (X, Y, and Z) are computed using the CIE Standard Observer functions. Using the weighted-ordinate method, tristimulus values are obtained from the following equations:

$$X = \sum_{400}^{700} R_\lambda x_\lambda, \quad Y = \sum_{400}^{700} R_\lambda y_\lambda, \quad Z = \sum_{400}^{700} R_\lambda z_\lambda,$$

where $R_\lambda$ is the percent reflectance of the object at wavelength $\lambda$ and $\bar{x}\lambda$, $\bar{y}\lambda$, and $\bar{z}\lambda$ are the Standard Observer functions at wavelength $\lambda$ for CIE Illuminant D65. The tristimulus values, X, Y and Z, identify the color of the object in terms of the mixture of the primary lights that match it visually. Tristimulus values, however, are of limited use as color specifications, because they do not correlate with visually meaningful attributes of color appearance and are not uniform in the spacing of colors as related to visual difference. As a result, "Uniform Color Scales" (UCS) have been adopted which use simple equations to approximate visual response. The UCS scale used by the Diano instrument is the CIE 1976 L*a*b* formula which converts tristimulus values to L*, a*, and b* values as shown below:

$$L^* = 25(100Y/Y_o)^{\frac{1}{3}} - 16$$
$$a^* = 500[(X/X_o)^{\frac{1}{3}} - (Y/Y_o)^{\frac{1}{3}}]$$
$$b^* = 200[(Y/Y_o)^{\frac{1}{3}} - (Z/Z_o)^{\frac{1}{3}}]$$

The L*-value is a measure of the luminosity or whiteness of an object where L*=100 is pure white, L*=0 is black, and in between is gray. The L*-value is strictly a function of the tristimulus Y-value. The b*-value is measure of the yellowness-blueness attribute where positive b*-values represent yellow appearance and negative b*-values represent blue appearance. The b*-value is a function of both tristimulus values Y and Z.

However, the variable nature of the impure isophthalic acid feedstock makes process control and thus quality assurance difficult and costly. For example, the commercial specifications for purified isophthalic acid may include a predetermined b*-value and/or optical density, and deviations from the predetermined b*-value and/or optical density that are either above or below the predetermined b*-value and/or optical density are undesirable. For this reason, it is highly desirable, and it is an object of the invention, to effect hydrogenation of an impure isophthalic acid solution under conditions that optimize control of the reduction of colored compounds. The present invention provides a convenient method for accomplishing this objective.

The following are believed to be relevant prior art disclosures:

Puskas et al., U.S. Pat. Nos. 4,394,299 and 4,467,110 disclose the use of a combination noble metal catalyst, for example, a palladium/rhodium catalyst on a porous carbonaceous surface, for purification of aqueous terephthalic acid solutions. These two patents also show the use of a rhodium-on-carbon catalyst under reducing conditions and review various heretofore known methods of preparing a Group VIII metal catalyst having activity and selectivity suitable for the purification of terephthalic acid by hydrogenating its principal impurity, 4-carboxybenzaldehyde, to p-toluic acid.

Schroeder et al. copending application Ser. No. 344,657, discloses a method for the purification of crude terephthalic acid, in which an aqueous solution of the crude terephthalic acid, at a temperature of from about 100° C. to about 350° C. and at a pressure sufficient to maintain the solution substantially in the liquid phase, is passed through a particulate catalyst bed and in the presence of hydrogen. The particulate catalyst bed is a layered bed that includes a first catalyst layer supported on an active carbon carrier and containing a metal of Group VIII of the Period Table of Elements having a single electron in its outermost orbital when in the ground state, and a lower catalyst layer containing palladium supported on an active carbon carrier. The solution is passed first through said first layer and thereafter through the second layer. Thereafter the hydrogenated aqueous solution is cooled to effect separation of the resulting purified terephthalic acid from the solution by crystallization.

Packer et al., U.S. Pat. No. 4,626,598, discloses a continuous method for producing purified terephthalic by the catalytic hydrogenation of crude terephthalic acid solution at 530-550° F. in a polar solvent in a reactor in which the solution hydrogen concentration is modulated during the hydrogenation so as to maintain a predetermined color scale b*-value in the resulting purified terephthalic acid. More particularly, the process involves recovering purified terephthalic acid from its solution, which had been hydrogenated at a given reactor hydrogen partial pressure measuring the color scale b*-value of the recovered purified terephthalic acid, and then based on the measured color scale b*-value, adjusting the reactor hydrogen partial pressure from the given reactor hydrogen partial pressure to provide purified terephthalic acid having a predetermined color scale b*-value. The hydrogen partial pressure within the reactor is maintained within the range of from about 10 to about 100 psi. A 0.1-unit change in the color scale b*-value can be effected by an adjustment of the hydrogen partial pressure from about 5 psi to about 60 psi. In the alternative, the optical density at 340 nanometers of a solution of the purified terephthalic acid which had been produced at a given reactor hydrogen partial pressure is measured and then based on the measured optical density, the reactor hydrogen partial pressure is adjusted from the given reactor hydrogen partial pressure to provide a purified terephthalic acid solution having a purified optical density. For 0.1-unit change in the optical density can be effected by an adjustment of the hydrogen partial pressure in the range of from about 2.5 psi to about 25 psi. For either of these alternatives when the hydrogenation is performed in a hydraulically full reactor, instead of adjusting the reactor hydrogen partial pressure from a given reactor hydrogen partial pressure, the gaseous hydrogen flow rate to the reactor can be adjusted from a given gaseous hydrogen flow rate to the reactor. A 0.1-unit change in the optical density can be effected by an adjustment in the solution hydrogen concentration in the range of from about 0.015 to about 0.15 cubic centimeters at 1 atmosphere absolute and 0° C. per gram. It is especially important to note that Packer et al. disclose that the b*-value and/or optical density of purified terephthalic acid are decreased by increasing the solution hydrogen concentration.

Schroeder et al. copending application Ser. No. 257,511, filed Oct. 13, 1988 discloses a method for the purification of crude isophthalic acid in which aqueous solution of said crude isophthalic acid, at a temperature of from about 100° C. to about 300° C. and at a pressure that is sufficient to maintain the solution substantially in the liquid phase, is passed through a particulate catalyst bed and in the presence of hydrogen. The particulate catalyst bed comprises Group VIII noble metal-containing components comprising at least two of palladium-, platinum-, rhodium-, ruthenium-, osmium- and iridium-containing components, supported on active carbon carrier particles. Thereafter the resulting hydrogenated aqueous solution is cooled to effect separation of the resulting purified isophthalic acid from the solution by crystallization.

SUMMARY OF THE INVENTION

The present invention is a method for the purification of crude isophthalic acid, comprising: hydrogenating a solution of said crude isophthalic acid with hydrogen in a polar solvent in a reaction at a temperature of from about 100° C to about 300° C and at a pressure that is sufficient to maintain the solution substantially in the liquid phase and in the presence of a catalyst comprising (a) a single Group VIII noble metal-containing component other than palladium or (b) a plurality of Group VIII noble metal-containing components comprising at least two of palladium-, platinum-, rhodium-, ruthenium-, osmium- and iridium-containing components, supported on active carbon carrier particles; modulating the solution hydrogen concentration during said hydrogenation so as to provide purified isophthalic acid having a predetermined color scale b*-value or optical density; and thereafter cooling the resulting hydrogenated solution to effect crystallization tion of the resulting purified isophthalic acid from the said solution.

DETAILED DESCRIPTION INCLUDING PREFERRED EMBODIMENTS

The method of this invention is particularly suitable for use in the purification of crude isophthalic acid prepared by the continuous catalytic, liquid-phase oxidation of m-xylene in a solvent. Suitable solvents for use in the catalytic, liquid-phase oxidation of m-xylene include any aliphatic $C_2-C_6$ monocarboxylic acid such as acetic acid, propionic acid, n-butyric acid, isobutyric acid, n-valeric acid, trimethylacetic and caproic acid, and water and mixtures thereof. Preferably, the solvent is a mixture of acetic acid and water, which more preferably contains from 1 to 20 weight percent of water, as introduced into the oxidation reactor. Since heat generated in the highly exothermic liquid-phase oxidation is dissipated at least partially by vaporization of solvent in the oxidation reactor, some of the solvent is withdrawn from the reactor as a vapor, which is then condensed and recycled to the reactor. In addition, some solvent is withdrawn from the reactor as a liquid in the product stream. After separation of the crude isophthalic acid product from the product stream, at least a portion of the mother liquor (solvent) in the resulting product stream is generally recycled to the reactor.

The source of molecular oxygen employed in the oxidation step of the method for producing purified isophthalic acid can vary in molecular oxygen content from that of air to oxygen gas. Air is the preferred source of molecular oxygen. In order to avoid the formation of explosive mixtures, the oxygen-containing gas fed to the reactor should provide an exhaust gas-vapor mixture containing from 0.5 to 8 volume percent oxygen (measured on a solvent-free basis). For example, a feed rate of the oxygen-containing gas sufficient to provide oxygen in the amount of from 1.5 to 2.8 moles per methyl group will provide such 0.5 to 8 volume percent of oxygen (measured on a solvent-free basis) in the gas-vapor mixture in the condenser.

The catalyst employed in the oxidation step of the method for producing crude isophthalic acid comprises cobalt, manganese, and bromine components, and can additionally comprise accelerators known in the art. The weight ratio of cobalt (calculated as elemental cobalt) in the cobalt component of the catalyst-to-m-xylene in the liquid-phase oxidation is in the range of from about 0.2 to about 10 milligram atoms (mga) per gram mole of m-xylene. The weight ratio of manganese (calculated as elemental manganese) in the manganese component of the catalyst-to-cobalt (calculated as elemental cobalt) in the cobalt component of the catalyst in the liquid-phase oxidation is in the range of from about 0.2 to about 10 mga per mga of cobalt. The weight ratio of bromine (calculated as elemental bromine) in the bromine component of the catalyst-to-total cobalt and manganese (calculated as elemental cobalt and elemental manganese) in the cobalt and manganese components of the catalyst in the liquidphase oxidation is in the range of from about 0.2 to about 1.5 mga per mga of total cobalt and manganese.

Each of the cobalt and manganese components can be provided in any of its known ionic or combined forms that provide soluble forms of cobalt, manganese, and bromine in the solvent in the reactor. For example, when the solvent is an acetic acid medium, cobalt and/or manganese carbonate, acetate tetrahydrate, and/or bromine can be employed. The 0.2:1.0 to 1.5:1.0 bromine-to-total cobalt and manganese milligram atom ratio is provided by a suitable source of bromine. Such bromine sources include elemental bromine ($Br_2$), or ionic bromide (for example, HBr, NaBr, KBr, $NH_4Br$, etc.), or organic bromides which are known to provide bromide ions at the operating temperature of the oxidation (e.g., bromobenzenes, benzylbromide, mono- and di-bromoacetic acid, bromoacetyl bromide, tetrabromoethane, ethylene-di-bromide, etc.). The total bromine in molecular bromine and ionic bromide is used to determine satisfaction of the elemental bromine-to-total cobalt and manganese milligram atom ratio of 0.2:1.0 to 1.5:1.0. The bromine ion released from the organic bromides at the oxidation operating conditions can be readily determined by known analytical means. Tetrabromoethane, for example, at operating temperatures of 170° C. to 225° C. has been found to yield about 3 effective gram atoms of bromine per gram mole.

In operation, the minimum pressure at which the oxidation reactor is maintained is that pressure which will maintain a substantial liquid phase of the m-xylene and at least 70 percent of the solvent. The m-xylene and solvent not in the liquid phase because of vaporization are removed from the oxidation reactor as a vapor-gas mixture, condensed, and then returned to the oxidation reactor. When the solvent is an acetic acid-water mixture, suitable reaction gauge pressures in the oxidation reactor are in the range of from about 0 kg/cm$^2$ to about 35 kg/cm$^2$, and typically are in the range of from about 10 kg/cm$^2$ to about 30 kg/cm$^2$. The temperature range within the oxidation reactor is generally from about 120° C., preferably from about 150° C., to about 240° C. The solvent residence time in the oxidation reactor is generally from about 20 to about 150 minutes and preferably from about 30 to about 120 minutes.

The resulting product is a slurry of relatively impure or crude isophthalic acid that includes relatively large amounts of impurities such as 3-carboxybenzaldehyde, which impurities can be present in amounts up to about 10,000 parts per million parts of isophthalic acid, by weight. These impurities adversely affect the isophthalic acid polymerization reactions which produce unsaturated polyesters as well as may cause undesirable coloring of the resulting unsaturated polyester polymers.

The process embodying the present invention is conducted at an elevated temperature and pressure in a fixed catalyst bed. Both down-flow and up-flow reactors can be used. The crude isophthalic acid to be purified is dissolved in water or a like polar solvent. Water is the preferred solvent; however, other suitable polar solvents are the relatively lower molecular weight alkyl carboxylic acids, alone or admixed with water. Hydrogenation of 3-carboxybenzaldehyde to m-toluic acid is one of the principal reactions that occur in the catalyst bed.

Reactor, and thus isophthalic acid solution, temperatures during purification can be in the range of about 100° C. (about 212° F.) to about 300° C. (about 572° F.). Preferably the temperatures are in the range of about 150° C. (about 302° F.) to about 250° C. (about 482° F.).

Reactor pressure conditions primarily depend upon the temperature at which the purification process is carried out. Inasmuch as the temperatures at which practical amounts of the impure isophthalic acid may be dissolved are substantially above the normal boiling point of the polar solvent, the process pressures are necessarily considerably above atmospheric pressure to maintain the isophthalic acid solution in liquid phase. If the reactor has a head space, the reactor pressure can be maintained by gaseous hydrogen alone or in admixture with an inert gas such as water vapor and/or nitrogen in the head space. The use of an inert gas in admixture with hydrogen also can provide an advantageous means for modulating the reactor hydrogen partial pressure, especially at relatively low hydrogen partial pressures. To this end, the inert gas preferably is admixed with hydrogen prior to introduction into the reactor. In general, the reactor pressure during hydrogenation can be in the range of about 100 to about 1000 pounds per square inch gauge (psig), and usually is in the range of about 350 psig to about 450 psig.

The hydrogenation reactor can be operated in several modes. For example, a predetermined liquid level can be maintained in the reactor and hydrogen can be fed in, for any given reactor pressure, at a rate sufficient to maintain the predetermined liquid level. The difference between the actual reactor pressure and the vapor pressure of the isophthalic acid solution present is the hydrogen partial pressure in the reactor vapor space. Alternatively, if hydrogen is fed in admixture with an inert gas such as nitrogen, the difference between the actual reactor pressure and the vapor pressure of the isophthalic acid solution present is the combined partial pressure of hydrogen and the inert gas admixed therewith. In this case the hydrogen partial pressure can be calculated from the known relative amounts of hydrogen and inert gas present in the admixture.

In the operating mode where process control is effected by adjusting the hydrogen partial pressure, the hydrogen partial pressure in the reactor preferably is in the range of about 10 psi to about 200 psi, or higher, depending upon the service pressure rating of the reactor, the degree of contamination of the impure isophthalic acid, the activity and age of the particular catalyst employed, and like processing considerations.

A suitable palladium-on-carbon catalyst can be obtained, for example, from Engelhard Corporation, Newark, N.J., under the designation "Palladium on Activated Carbon Granules (Carbon Code CG-5)." Similarly, suitable rhodium-on-carbon catalysts can be obtained from Engelhard Corporation, under the designations "Rhodium on Activated Carbon Granules (Carbon Code CG-5)" and "Rhodium on Activated Carbon Granules (Carbon Code CG-21)." Both of these rhodium-on-carbon catalysts have a N$_2$ BET surface area of about 1,000 m$^2$/gram and have a particle size of 4×8 mesh, U.S. Sieve Series. Other suitable rhodium-on-carbon and palladium-on-carbon catalysts of similar size and surface area are available from Johnson Matthey Inc., Seabrook, N.H., under the designation "11766 Rhodium, 1% on Steam Activated Carbon Granules, Anhydrous." Similarly, suitable ruthenium-on-carbon, platinum-on-carbon and iridium-on-carbon catalysts are also commercially available.

The catalyst carrier is active carbon, usually that derived from coconut charcoal in the form of granules having a surface area of at least about 600 m$^2$/g (N$_2$; BET Method), preferably about 800 m$^2$/g to about 1,500 m$^2$/g. However, other porous carbonaceous supports or substrates can be used as long as the surface area requirements can be met. In addition to coconut charcoal, activated carbon derived from other plant or from animal sources can be utilized.

The loading of each of the palladium, ruthenium, rhodium, platinum, osmium or iridium employed on the carrier is in the range of about 0.01 weight percent to about 2 weight percent, based on the total weight of the catalyst, i.e., metal plus active carbon carrier, and calculated as elemental metal. Preferably the loading of each catalyst metal employed is about 0.5 weight percent.

In one embodiment of the method of the present invention, the Group VIII noble metal-containing components are supported on the same active carbon carrier particles and thus there is a substantially uniform distribution of each of the Group VIII noble metal-containing components throughout the catalyst bed. In this embodiment, a particular active carbon carrier particle contains all of the Group VIII noble metal-containing components, and the relative amounts of the Group VIII noble metals in the catalyst bed are controlled by the relative amounts of the two Group VIII noble metals on each catalyst particle.

In the alternative, and preferably, one of the Group VIII noble metal-containing components is supported on a first group of the active carbon carrier particles, and a second Group VIII noble metal-containing component is supported on a second group of the active carbon carrier particles, and the aforesaid first group of particles is separate and distinct from the aforesaid second group of particles. In this embodiment, a particular active carbon carrier particle contains only one Group VIII noble metal-containing component; and the relative amounts of the Group VIII noble metals in the catalyst bed are controlled either by the relative amounts of the Group VIII noble metal-containing components employed in their respective groups of active carbon carrier particles or by the relative amounts of active carbon carrier particles employed in their respective groups of active carbon carrier particles. In this embodiment, when each of the first and second groups of active carbon carrier particles are uniformly distributed throughout the catalyst bed, the Group VIII noble metal-containing components are also uniformly distributed throughout the catalyst bed. Alternatively in this embodiment, the catalyst bed is layered and has (1) at least one layer comprising substantially only the aforesaid first group of particles and (2) at least one layer comprising substantially only the aforesaid second group of particles, and thus the Group VIII noble metal-containing components are not uniformly distributed throughout the catalyst bed.

In this later case of a layered bed, the isophthalic acid solution is passed first through a first layer comprising substantially only the aforesaid first group of particles containing only a first Group VIII noble metal-containing component and then through a second layer comprising substantially only the aforesaid second group of particles containing only the second Group VIII noble metal-containing component. Typically the weight ratio of the first layer to the second layer is in the range of from about 1:100, preferably from about 1:20, to about 1:2, preferably to about 1:4. Similarly the residence time of the aqueous isophthalic acid solution in the first layer is from about 1:2 to about 1:100 of the total residence time of the solution in the catalyst bed. Thereafter the aqueous solution is withdrawn from the catalyst bed directly or after passing the aqueous solution through a third layer comprising, for example, substantially only either the aforesaid first group of particles containing only the first Group VIII noble metal-containing component or a third group of particles comprising a third Group VIII noble metal-containing component.

In the method of the present invention, the hydrogen concentration of the solution of crude isophthalic acid is modulated during hydrogenation so as to provide purified isophthalic acid having a predetermined color scale b*-value or a predetermined optical density, and thereafter the resulting hydrogenated solution is cooled so as to effect crystallization of the resulting purified isophthalic acid. Surprisingly, in contrast to the purification of terephthalic acid disclosed in Packer et al., U.S. Pat. No. 4,626,598, in the method of the present invention, the solution hydrogen concentration during hydrogenation is adjusted upwardly or downwardly in order to provide purified isophthalic acid having a higher or lower, respectively, predetermined color scale b*-value or predetermined optical density.

The aforesaid modulation of the solution hydrogen concentration can be effected in a number of different ways.

For example, in one embodiment, when the hydrogenation is being performed at a given hydrogen partial pressure in the purification reactor, the purified isophthalic acid produced at this given hydrogen partial pressure is crystallized and separated from the resulting hydrogenated solution, and the color scale b*-value, or the optical density in ammonia solution at 340 or 400 nanometers, of the recovered purified isophthalic acid is determined. Then, based on this determined color scale b*-value or determined optical density, the hydrogen partial pressure under which the hydrogenation is performed in the purification reactor is adjusted so as to provide purified isophthalic acid having a predetermined color scale b*-value or predetermined optical density. Typically, the hydrogen partial pressure within the purification reactor is maintained within the range of from about 10 to about 200 pounds per square inch absolute. In general, under these conditions, an adjustment of the hydrogen partial pressure within the purification reactor of from about 5 to about 60 pounds per square inch is sufficient to implement a 0.1-unit change in either the color scale b*-value or the optical density.

In alternative embodiment, instead of adjusting the hydrogen partial pressure in the purification reactor—for example, when the purification reactor is hydraulically full—the gaseous hydrogen flow rate to the purification reactor is adjusted from an initial or given flow rate so as to provide purified isophthalic acid having a predetermined color scale b*-value or a predetermined optical density. The change in the gaseous hydrogen flow rate to the purification reactor can be based either on a determined (that is, measured) color scale b*-value or determined (that is, measured) optical density of isophthalic acid after it has been purified at the given or initial gaseous hydrogen flow rate and then separated from the hydrogenated solution. Typically, an adjustment of the gaseous hydrogen flow rate to the purification reactor in the range of about 0.015 to about 0.3 cubic centimeters at 1 atmospheric (absolute) and 0° C. per gram is sufficient to implement a 0.1-unit change in the color scale b*-value. Expressed differently, an adjustment of the gaseous hydrogen flow rate to the purification reactor in the range of from about 0.015 to about 0.3 cubic centimeter at 1 atmosphere (absolute) and 0° C. per gram for a 0.1-unit change in the optical density.

Runs were performed on a batch basis in a one-gallon titanium autoclave to study the effect of varying the hydrogen partial pressure in the purification of crude isophthalic acid. In each run, a liquid solution of 450 grams of crude isophthalic acid in 1050 grams of water was heated in the reactor to 232° C. and at either 43 or 172 pounds per square inch absolute of hydrogen partial pressure and then 2 grams of catalyst particles of a Group VIII noble metal on granular carbon were introduced into the solution in the reactor. A palladium-on-carbon catalyst was employed for one series of runs, and a rhodium-on-carbon catalyst was employed for a second series of runs. In each case, the catalyst contained 0.5 weight percent of the noble metal, calculated as the elemental metal and based on the total weight of the catalyst.

A 40 gram sample of the solution was withdrawn from the reactor at time intervals of 0, 10, 20, 30, 60, 120, 180 and 240 minutes after addition of the catalyst. Each sample was heated to dryness at 110° C. in a vacuum oven, and then its color scale b*-value was determined and also the optical density at each of 340 nanometers and 400 nanometers of the ammonia solution of each dried sample was determined.

The results of these analyses are presented in Table 1. In Table 1, low P and high P refer to the low and higher hydrogen partial pressures employed and the time indicated is the time when the sample was withdrawn.

TABLE 1

| Time | b*-value | | OD-340 | | OD-400 | |
|---|---|---|---|---|---|---|
| (min.) | low P | high P | low P | high P | low P | high P |
| Rhodium Catalyst | | | | | | |
| 0 | 2.98 | 2.91 | 1.63 | 1.41 | 0.230 | 0.185 |
| 10 | 1.84 | 2.43 | 1.28 | 2.02 | 0.140 | 0.350 |
| 20 | 1.39 | 2.17 | 1.11 | 2.03 | 0.105 | 0.390 |
| 30 | 1.09 | 2.37 | 0.96 | 1.88 | 0.085 | 0.395 |
| 60 | 0.96 | 2.19 | 0.91 | 2.15 | 0.085 | 0.465 |
| 120 | 0.95 | 2.34 | 0.85 | 1.73 | 0.065 | 0.390 |
| 180 | 0.93 | 2.34 | 0.76 | 1.97 | 0.053 | 0.450 |
| 240 | 0.70 | 2.54 | 0.71 | 2.08 | 0.045 | 0.505 |
| Palladium Catalyst | | | | | | |
| 0 | 1.98 | 2.70 | 1.47 | 1.45 | 0.185 | 0.170 |
| 10 | 1.99 | 1.97 | 1.33 | 1.23 | 0.160 | 0.180 |
| 20 | 1.53 | 1.73 | 1.17 | 1.35 | 0.135 | 0.175 |
| 30 | 1.45 | 1.58 | 1.09 | 1.07 | 0.105 | 0.160 |
| 60 | 1.26 | 1.51 | 0.97 | 0.97 | 0.100 | 0.155 |
| 120 | 1.29 | 1.53 | 0.94 | 0.87 | 0.105 | 0.135 |
| 180 | 1.13 | 1.58 | 0.89 | 0.85 | 0.110 | 0.145 |
| 240 | 1.46 | 1.48 | 0.83 | 0.76 | 0.100 | 0.120 |

TABLE 1-continued

A run was also made in a commercial unit for the continuous purification of crude isophthalic acid. In the run, the aqueous solvent, temperature, total pressure and overall space velocity (weight of crude isophthalic acid per weight of total catalyst per hour) employed in the purification reaction are all within the classes and ranges described therefor generally hereinabove, and were each maintained constant throughout the run. In the run, the bed of catalyst particles contained a lower layer of palladium-on-carbon catalyst particles containing 0.5 weight percent of palladium calculated as elemental palladium and having a total surface area of about 1000 m²/gm and having a particle size of 4 to 8 mesh. An upper layer of rhodium-on-carbon catalyst particles was placed on the top of the palladium-on-carbon particles and contained 0.5 weight percent of rhodium, calculated as elemental rhodium, and had a total surface area of about 1000 m²/gm and a particle size of 4 to 8 mesh. The total weight of the rhodium-on-carbon particles was about 14 percent of the total weight of the palladium-on-carbon particles.

An aqueous solution of the crude isophthalic acid was introduced into the top portion of the purification reactor and flowed downward from the top to the bottom of the catalyst bed. The hydrogen partial pressure in the reactor was increased gradually and in a stepwise fashion over the length of the run from 40 to 120 pounds per square inch absolute and b*-value of the resulting purified isophthalic acid increased as follows: 0.66, 0.68, 0.75, 0.72, 0.91, 0.85, and 1.06 units at 40, 60, 67, 81, 93, 106 and 123 psia, respectively, of hydrogen partial pressure.

The results of the runs in the autoclave and in the commercial unit illustrate that when palladium is employed as the purification catalyst, there is little or no effect of the solution hydrogen concentration on the b*-value or the optical density measured at either 340 or 400 nanometers. By contrast, when either rhodium alone or a combination of two Group VIII noble metals are employed as the purification catalyst, the use of the lower solution hydrogen concentration in the purification affords a substantial reduction in the b*-value and optical densities measured at both 340 and 400 nanometers.

From the above description, it is apparent that the object of the present invention has been achieved. While only certain embodiments have been set forth, alternative embodiments and various modifications will be apparent from the above description to those skilled in the art. These alternatives are considered equivalent and are within the spirit and scope of the present invention.

Having described the invention, what is claimed is:

1. A method for the purification of crude isophthalic acid, comprising: hydrogenating a solution of said crude isophthalic acid in a polar solvent with hydrogen in a reactor at a temperature of from about 100° C. to about 300° C., at a pressure that is sufficient to maintain the solution substantially in the liquid phase, and in the presence of a catalyst comprising (a) a single Group VIII noble metal-containing component other than palladium or (b) a plurality of Group VIII noble metal-containing components comprising at least two of palladium-, platinum-, rhodium-, ruthenium-, osmium- and iridium-containing components, supported on active carbon carrier particles;

modulating the solution hydrogen concentration during said hydrogenation so as to provide purified isophthalic acid having a predetermined color scale b*-value or optical density; and thereafter cooling the resulting hydrogenated solution to effect crystallization from the said solution of the resulting purified isophthalic acid having the predetermined b*-value or optical density.

2. The method of claim 1 wherein the solution hydrogen concentration during hydrogenation is adjusted upwardly or downwardly in order to provide purified isophthalic acid having a higher or lower, respectively, predetermined color scale b*-value or optical density.

3. The method of claim 1 wherein the solution of crude isophthalic acid is passed through a particulate catalyst bed and the bed comprises a plurality of Group VIII noble metal-containing components comprising at least two of palladium-, platinum-, rhodium-, ruthenium-, osmium-, and iridium-containing components supported on active carbon carrier particles.

4. The method of claim 3 wherein each of the plurality of Group VIII noble metal-containing components is supported on the same active carbon carrier particles and there is a substantially uniform distribution of each of the Group VIII noble metal-containing components throughout the catalyst bed.

5. The method of claim 3 wherein one of the Group VIII noble metal-containing components is supported on a first group of the active carbon carrier particles and a second Group VIII noble metal-containing component is supported on a second group of the active carbon carrier particles, and the aforesaid first group of particles is separate and distinct from the aforesaid second group of particles.

6. The method of claim 5 wherein the first and second groups of particles are substantially uniformly distributed throughout the catalyst bed.

7. The method of claim 5 wherein the catalyst bed is layered and has at least one layer comprising substantially only the aforesaid first group of particles and at least one layer comprising substantially only the aforesaid second group of particles.

8. The method of claim 7 wherein the solution is passed first through a first layer comprising substantially only the aforesaid first group of particles and then through a second layer comprising substantially only the aforesaid second group of particles.

9. The method of claim 6 wherein after being passed through the second layer and before being withdrawn from the catalyst bed, the solution is passed through a third layer comprising substantially only either the aforesaid first group of particles or a third group of particles comprising a third Group VIII noble metal-containing component.

10. The method of claim 1 wherein the isophthalic solution is maintained at a temperature of about 150° C. to about 250° C., and wherein hydrogen is present in an amount of about twice the amount stoichiometrically required to hydrogenate all hydrogenatable impurities.

11. The method of claim 3 wherein the space velocity of the isophthalic acid solution through the catalyst bed is about 5 hours$^{-1}$ to about 25 hours$^{-1}$.

12. The method of claim 11 wherein the space velocity of the aqueous isophthalic acid solution through the catalyst bed is about 10 hours$^{-1}$ to about 25 hours$^{-1}$.

13. The method of claim 8 wherein the residence time of the isophthalic acid solution in said first layer is from about 1:100 to about 1:2 of the total residence time of the aqueous isophthalic acid solution in the particulate catalyst bed.

14. The method of claim 1 wherein said Group VIII noble metals are at least two of palladium, rhodium, platinium, ruthenium, osmium, or iridium.

15. The method of claim 14 wherein said Group VIII noble metals comprise palladium and rhodium.

16. The method of claim 3 wherein each Group VIII noble metal is present in the catalyst bed at a same or different concentration in the range of from about 0.01 to about 2 percent by weight, based on the weight of the catalyst bed and calculated as the elemental metal.

17. The method of claim 3 wherein two Group VIII noble metals are present in the catalyst bed at an atomic ratio in the range of from about 1:100 to about 1:1, calculated as the elemental metals.

18. The method of claim 17 wherein the aforesaid two Group VIII noble metals are present in the catalyst bed at an atomic ratio in the range of from about 1:20 to about 1:4, calculated as the elemental metals.

19. The method of claim 8 wherein the first group of particles comprises a rhodium-containing component and the second group of particles comprises a palladium-containing component.

20. The method of claim 8 wherein the first group of particles comprises a palladium-containing component and the second group of particles comprises a rhodium-containing component.

21. The method of claim 1 wherein water is the polar solvent.

22. The method of claim 1 wherein, in the aforesaid modulation,
(a) the hydrogenation is performed at a given reactor hydrogen partial pressure;
(b) the resulting purified isophthalic acid is recovered from the resulting hydrogenated solution;
(c) either the color scale b*-value of the recovered purified isophthalic acid or the optical density of an ammonia solution of the recovered purified isophthalic acid is determined; and
(d) based on the aforesaid determined color scale b*value or determined optical density, the reactor hydrogen partial pressure under which the hydrogenation is performed is adjusted to provide purified isophthalic acid having a predetermined color scale b*-value or a predetermined optical density, respectively.

23. The method of claim 22 wherein the hydrogen partial pressure within the reactor is maintained within the range of about 10 to about 200 pounds per square inch absolute.

24. The method of claim 22 wherein the hydrogen partial pressure within the reactor is adjusted about 5 psia to about 60 psia for a 0.1 unit change in the color scale b*-value to be implemented.

25. The method of claim 22 wherein the reactor hydrogen partial pressure is adjusted about 5 psia to about 60 psia for a 0.1-unit change in the optical density.

26. The method of claim 1 wherein, in the aforesaid modulation,
(a) the hydrogenation is performed at a given gaseous hydrogen flow rate to the reactor;

(b) the resulting purified isophthalic acid is recovered from the resulting hydrogenated solution;
(c) either the color scale b*-value of the recovered purified isophthalic acid or the optical density of an ammonia solution of the recovered purified terephthalic acid is determined; and
(d) based on the aforesaid determined color scale b*-value or determined optical density, the gaseous hydrogen flow rate to the reactor at which the hydrogenation is performed is adjusted to provide purified isophthalic acid having a predetermined color scale b*-value or a predetermined optical density, respectively.

27. The method of claim 26 wherein the gaseous hydrogen flow rate to the reactor is adjusted to provide a change in solution hydrogen concentration in the range of about 0.015 to 0.3 cubic centimeters at 1 atmosphere (absolute) and 0° C. per gram of crude isophthalic acid solution introduced into the reactor for a 0.1-unit change in the color scale b*-value to be implemented.

28. The method of claim 26 wherein the gaseous hydrogen flow rate to the reactor is adjusted to provide a change in solution hydrogen concentration in the range of about 0.015 to about 0.3 cubic centimeters at 1 atmosphere (absolute) and 0° C. per gram of crude isophthalic acid solution introduced into the reactor for a 0.1 unit change in the optical density to be implemented.

* * * * *

UNITED STATES PATENT OFFICE
CERTIFICATE OF CORRECTION

Patent No. 4,937,378　　　　　　　　　　　Dated June 26, 1990

Inventor(s)　　Hobe Schroeder

It is certified that error appears in the above-identified patent and that said Letters Patent is hereby corrected as shown below:

| Col. | Line | |
|---|---|---|
| 1 | 14 | "osmium" should read --osmium-- |
| 2 | 3 | "$x_\lambda \ldots y_\lambda \ldots z_\lambda$" should read --$\bar{x}_\lambda \ldots \bar{y}_\lambda \ldots \bar{z}_\lambda$-- |
| 2 | 14 | "difference" should read --differences-- |
| 2 | 6 | "$\bar{x}_\lambda, \bar{y}_\lambda,$ and $\bar{z}_\lambda$" should read --$\bar{x}_\lambda, \bar{y}_\lambda,$ and $\bar{z}_\lambda$-- |
| 4 | 23 | "crystallization tion of" should read --crystallization of-- |
| 8 | 6-7 | "metalcontaining" should read --metal-containing-- |
| 9 | 11 | "rate .to" should read --rate to-- |
| 10 | 20 | "rhodi-um" should read --rhodium-- |
| 10 | 25 | should read --rhodium-- |
| 10 | 35 | "and b*-value" should read --and the b*-value-- |
| 12 | 48 | "b*value" should read --b*-value-- |

Signed and Sealed this

Twenty-ninth Day of October, 1991

*Attest:*

HARRY F. MANBECK, JR.

*Attesting Officer*　　　　*Commissioner of Patents and Trademarks*